(12) United States Patent
Zoppetti et al.

(10) Patent No.: US 7,423,028 B2
(45) Date of Patent: Sep. 9, 2008

(54) INJECTABLE PHARMACEUTICAL COMPOSITIONS COMPRISING SODIUM DICLOFENAC AND β-CYCLODEXTRIN

(75) Inventors: Giorgio Zoppetti, Milan (IT); Nadia Puppini, Como (IT); Marco Pizzutti, Malnate (IT)

(73) Assignee: Ibsa Institut Biochemique S.A., Massagno (CH)

( * ) Notice: Subject to any disclaimer, the term of this patent is extended or adjusted under 35 U.S.C. 154(b) by 412 days.

(21) Appl. No.: 11/158,517

(22) Filed: Jun. 21, 2005

(65) Prior Publication Data

US 2005/0282776 A1   Dec. 22, 2005

(30) Foreign Application Priority Data

Jun. 22, 2004   (IT)   .............................. MI04A1245

(51) Int. Cl.
*A61K 31/196* (2006.01)
*A61K 31/724* (2006.01)
*A61K 47/14* (2006.01)

(52) U.S. Cl. ........................ 514/58; 514/539; 514/772.2

(58) Field of Classification Search ....................... None
See application file for complete search history.

(56) References Cited

U.S. PATENT DOCUMENTS

| 5,554,650 | A | 9/1996 | Holl et al. .................... 514/567 |
| 6,365,180 | B1 | 4/2002 | Meyer et al. ................. 424/451 |
| 2002/0016359 | A1 * | 2/2002 | Hellberg et al. ............. 514/456 |

FOREIGN PATENT DOCUMENTS

| EP | 94308690 | 3/2000 |
| EP | 0658347 | 8/2003 |

OTHER PUBLICATIONS

Szente, L. et al "Highly soluble cyclodextrin derivatives . . . " Adv. Drug Deliv. Rev. (1999) vol. 36, pp. 17-28.*

* cited by examiner

*Primary Examiner*—Leigh C Maier
(74) *Attorney, Agent, or Firm*—Abelman, Frayne & Schwab

(57) ABSTRACT

Injectable pharmaceutical compositions are described comprising sodium diclofenac, a β-cyclodextrin and a polysorbate, suitable for subcutaneous and intramuscular administration.

5 Claims, 1 Drawing Sheet

INJECTABLE PHARMACEUTICAL COMPOSITIONS COMPRISING SODIUM DICLOFENAC AND β-CYCLODEXTRIN

FIELD OF THE INVENTION

The present invention refers to the field of pharmaceutical compositions and in particular to a new injectable pharmaceutical composition based on sodium diclofenac.

STATE OF THE ART

Sodium diclofenac i.e. 2-[(2,6-dichlorophenyl)amino] benzeneacetic acid monosodium salt, has a recognised anti-inflammatory activity and for this reason has long been used as the active principle in various types of pharmaceutical formulations used in treating painful conditions, including post-traumatic and post-operative, and in all rheumatic diseases.

Diclofenac acts by inhibiting the synthesis of prostaglandins, the principal cause of inflammation and pain. To achieve the maximum effectiveness in pain relief the active principle must reach the systemic circulation as soon as possible after administration, so consequently the injectable form has always been favoured particularly for the treatment of acute inflammations of the musculo-skeletal system.

Given that sodium diclofenac is a compound sparingly soluble in water, currently available injectable pharmaceutical formulations based on this active principle contain a quantity thereof equal to 75 mg dissolved in 3 ml of solvent, consisting of 30 volume % propylene glycol and 70 vol % water.

However, this formulation is not pleasant for the patient because it is painful; also, given the total volume of a single dose, administration is only possible by intramuscular or intravenous injections.

In order to overcome these problems which are due to the low solubility in water of diclofenac, compositions were prepared in which diclofenac or its salts are combined with cyclodextrins. As is indeed known from the literature on the subject, cyclodextrins increase the solubility of diclofenac, as they give rise to a water soluble complex with this active principle.

However, it is also known that even with the aid of hydroxypropyl-β-cyclodextrin, pharmaceutical compositions suitable for injecting cannot in any case be obtained should the concentration of sodium diclofenac need to be increased, for example from 25 mg/ml to 75 mg/ml, because crystals of sodium diclofenac can form, as illustrated for example in European Patent No. 658 347 B1.

Therefore the problem of identifying an injectable formulation having a sodium diclofenac concentration greater than 25 mg/ml but without the aforestated disadvantages of known pharmaceutical compositions, has not yet been solved.

SUMMARY

The Applicant has now found that by adding a polysorbate within very precise concentration limits to an aqueous solution containing a β-cyclodextrin and sodium diclofenac at a concentration higher than 25 mg/ml of water, crystal formation can be completely prevented, thus obtaining solutions which remain clear and stable in the long term, both at room temperature and at 4° C.

It is therefore subject of the present invention an injectable pharmaceutical composition in the form of an aqueous solution, comprising sodium diclofenac at a concentration greater than 25 mg/ml of water and a β-cyclodextrin, characterised in that it comprises at least a polysorbate in an amount ranging between 0.01 and 0.06% by weight with respect to the total volume of the solution.

The characteristics and advantages of the pharmaceutical compositions of the present invention will be illustrated in detail in the following description.

DETAILED DESCRIPTION OF THE INVENTION

Figure 1:
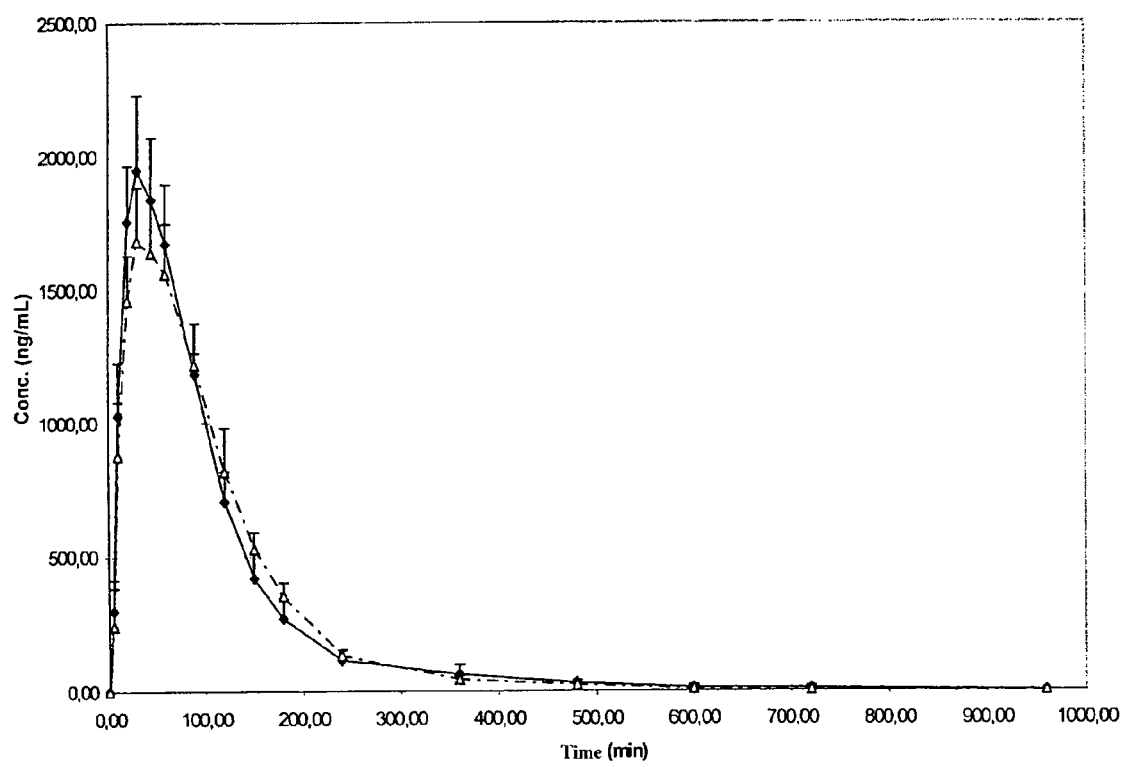
FIG. 1: shows the two curves of the plasma concentrations of sodium diclofenac vs. time, 960 minutes after intramuscular (—♦—) and subcutaneous (--Δ--) administration of the composition of Example 1, to three healthy volunteers.

In the pharmaceutical compositions of the invention the polysorbate preferably used is polysorbate 20, or polyoxyethylene sorbitan monolaurate, available on the market with the commercial name Tween® 20. The amount of polysorbate in the compositions of the invention must be between 0.01 and 0.06% by weight with respect to the total volume of the solution.

The Applicant has found that if the same polysorbate is used in concentrations outside the aforesaid range, a satisfying result in terms of composition stability is not achieved, either at room temperature or at 4° C.

As given hereinafter in the comparative example 2, polysorbate concentrations lower than 0.01% w/v give rise to unsatisfactory compositions in terms of diclofenac solubility at low temperatures; indeed, after a relatively brief storage period at 4° C., diclofenac crystals form in the solution. From the comparative example 3 given hereinafter, it is evident instead that polysorbate concentrations above 0.06% w/v give similarly unsatisfactory results in terms of solution stability, if stored at ambient temperature.

According to a particularly preferred embodiment of the present pharmaceutical compositions, the amount of polysorbate is equal to 0.05% by weight with respect to the total volume of the solution.

According to a preferred embodiment of the invention the molar ratio of sodium diclofenac to β-cyclodextrin ranges between 1:1 and 1:1.3.

The β-cyclodextrin is preferably hydroxypropyl β-cyclodextrin.

In addition to the active principle, cyclodextrin and polysorbate, the pharmaceutical compositions of the invention may also comprise pharmaceutically acceptable excipients chosen from those conventionally used in pharmaceutical compositions so as to achieve an injectable solution, which is injectable either by intramuscular or subcutaneous means, and useful for treating painful conditions. The compositions of the invention can be prepared in various formulations, in particular according to the preferred dosage unit of 75 mg sodium diclofenac.

The pharmaceutical compositions of the invention can be prepared by mixing an aqueous solution of polysorbate with an aqueous solution of cyclodextrin and then adding sodium diclofenac.

The pharmaceutical compositions, prepared in the form of aqueous solutions as aforedescribed, are found to be stable long-term, and have not shown crystal formation for at least three months after preparation, either at room temperature or at 4° C.

The following non-limiting examples of the invention are given for illustrative purposes.

EXAMPLE 1

Preparation of the sodium diclofenac and hydroxypropyl β-cyclodextrin complex with 0.05% w/v Tween® 20

The following two solutions are prepared:

Solution A: 1003 mg of Tween® 20 are dissolved in 20 ml of deionised water.

Solution B: 6.6 g of hydroxypropyl β-cyclodextrin are dissolved under stirring, in about 10 ml of deionised water, until a transparent colourless solution is obtained. 1.50 g of sodium diclofenac and 0.2 ml of Solution A prepared as aforedescribed are added to solution B, under stirring. The solution is then brought to a final volume of 20 ml with deionised water and placed under stirring for about 40 minutes.

After filtering through a 0.22 μm filter, a transparent colourless solution is obtained with a sodium diclofenac concentration which, by UV analysis, was found to be 72.91 mg/ml.

This solution, packed and stored in accordance with the usual procedures adopted for injectable pharmaceutical formulations, remained clear for more than 3 months without showing crystal formation, both at room temperature and at 4° C.

EXAMPLE 2 (COMPARATIVE)

Preparation of the sodium diclofenac and hydroxypropyl β-cyclodextrin complex with 0.005% w/v Tween® 20

The following two solutions are prepared:

Solution A: 100.3 mg of Tween® 20 are dissolved in 20 ml of deionised water.

Solution B: 6.6 g of hydroxypropyl β-cyclodextrin are dissolved in about 10.0 ml of deionised water under stirring, until a transparent colourless solution is obtained.

1.51 g of sodium diclofenac and 0.2 ml of solution A prepared as aforedescribed are added to solution B, under stirring. The solution is then brought to a final volume of 20 ml with deionised water and placed under stirring for about 40 minutes. The solution is then filtered through a 0.22 μm filter to obtain a transparent colourless solution with a sodium diclofenac content which, by UV analysis, was found to be 79.14 mg/ml.

This solution, packed and stored in accordance with the usual procedures adopted for injectable pharmaceutical formulations, remained clear for more than 3 months at room temperature without showing crystal formation, while at 4° C. the formation of diclofenac crystals, in acid and sodium salt forms, was observed after only 1 month.

EXAMPLE 3 (COMPARATIVE)

Preparation of the sodium diclofenac and hydroxypropyl β-cyclodextrin complex with 0.18% w/v Tween® 20 17.4 g of hydroxypropyl-β-cyclodextrin are dissolved in about 28 ml of deionised water under stirring, until a transparent colourless solution is obtained. 3.75 g of sodium diclofenac and 90.1 mg of Tween® 20 are added under stirring.

The solution is then brought to a final volume of 50 ml with deionised water and placed under stirring for about 40 minutes. The solution is then filtered through a 0.22 μm filter to obtain a transparent colourless solution with a sodium diclofenac concentration found to be 80.49 mg/ml, by UV analysis.

The solution was packed and stored in accordance with the usual procedures adopted for injectable pharmaceutical formulations. The solution stored at 4° C. remained clear, while a turbidity was observed in the same solution stored at room temperature after only one week of storage.

EXAMPLE 4

Subcutaneous pharmacokinetics in humans

The solution prepared as described above in Example 1 and containing 72.91 mg/ml of sodium diclofenac, was sterilized by the sterilizing filtration method under aseptic conditions in vials containing 75 mg of sodium diclofenac per unit.

A dose of the sterile solution (75 mg) was injected subcutaneously into the upper thighs of three healthy volunteers from whom a blood sample was taken prior to administration and at time intervals up to 960 minutes after administration.

In FIG. 1 the change in plasma sodium diclofenac levels with time is shown, indicated by the broken curve with triangles corresponding to the individual values found.

EXAMPLE 5

Intramuscular pharmacokinetics in humans

The solution prepared as described above in Example 1 and containing 72.91 mg/ml of sodium diclofenac, was sterilized by the sterilizing filtration method under aseptic conditions in vials containing 75 mg of sodium diclofenac per unit.

A dose of the sterile solution (75 mg) was injected intramuscularly into the upper thighs of three healthy volunteers from whom a blood sample was taken prior to administration and at time intervals up to 960 minutes after administration.

In FIG. 1 the change in plasma sodium diclofenac levels with time is shown, indicated by the continuous curve with lozenges corresponding to the individual values found.

The invention claimed is:

1. An injectable pharmaceutical composition in the form of an aqueous solution, comprising sodium diclofenac at a concentration of 75 mg/ml and hydroxypropyl-β-cyclodextrin, wherein said composition further comprises at least a polysorbate in an amount ranging between 0.01 and 0.06% by weight with respect to the total volume of the solution.

2. The pharmaceutical composition according to claim 1, wherein said polysorbate is polysorbate 20 (polyoxyethylene sorbitan monolaurate).

3. The pharmaceutical composition according to claim 1, wherein said polysorbate is present in an amount equal to 0.05% by weight with respect to the total volume of the solution.

4. The pharmaceutical composition according to claim 1, wherein the molar ratio of sodium diclofenac to hydroxypropyl-β-cyclodextrin is comprised between 1:1 and 1:1.3.

5. The pharmaceutical composition according to claim 1, in the form of a unit dose containing 75 mg of sodium diclofenac.

* * * * *

UNITED STATES PATENT AND TRADEMARK OFFICE
CERTIFICATE OF CORRECTION

| | | |
|---|---|---|
| PATENT NO. | : 7,423,028 B2 | Page 1 of 1 |
| APPLICATION NO. | : 11/158517 | |
| DATED | : September 9, 2008 | |
| INVENTOR(S) | : Zoppetti et al. | |

It is certified that error appears in the above-identified patent and that said Letters Patent is hereby corrected as shown below:

Title page, item (73) Assignee: should read: Altergon S.A.
6903 Lugano (CH)

Signed and Sealed this

Third Day of August, 2010

David J. Kappos
*Director of the United States Patent and Trademark Office*